United States Patent
Gilman et al.

[11] Patent Number: 5,811,116
[45] Date of Patent: Sep. 22, 1998

[54] ADHESIVE WAFER WITH EMBOSSED SKIN-CONTACTING SURFACE

[75] Inventors: Thomas H. Gilman, Spring Grove; Barry L. Schneider, McHenry; Eric D. Ellingson, Mount Prospect, all of Ill.

[73] Assignee: Hollister Incorporated, Libertyville, Ill.

[21] Appl. No.: 640,008

[22] Filed: Apr. 30, 1996

[51] Int. Cl.⁶ .......................... A61F 13/00; A61L 15/16
[52] U.S. Cl. .................. 424/443; 424/446; 424/447; 424/448; 424/449
[58] Field of Search .................. 424/443, 446, 424/447, 448, 449; 128/156

[56] References Cited

U.S. PATENT DOCUMENTS

| | | | |
|---|---|---|---|
| 3,081,771 | 3/1963 | Lee | 128/283 |
| 3,457,919 | 7/1969 | Harbard | 128/156 |
| 3,941,133 | 3/1976 | Chen | 128/283 |
| 4,341,207 | 7/1982 | Steer et al. | 128/155 |
| 4,699,792 | 10/1987 | Nick et al. | 424/446 |
| 4,773,408 | 9/1988 | Cilento et al. | 128/156 |
| 4,865,594 | 9/1989 | Thomas | 604/332 |
| 4,921,704 | 5/1990 | Fabo | 424/446 |
| 4,995,382 | 2/1991 | Lang et al. | 128/156 |
| 5,051,259 | 9/1991 | Olsen et al. | 424/443 |
| 5,123,900 | 6/1992 | Wick | 602/41 |
| 5,244,457 | 9/1993 | Karami et al. | 602/55 |
| 5,607,413 | 3/1997 | Holmberg et al. | 604/342 |
| 5,709,673 | 1/1998 | Keyes | 604/332 |
| 5,716,475 | 2/1998 | Botten et al. | 156/219 |

FOREIGN PATENT DOCUMENTS

| | | |
|---|---|---|
| 0 409 587A | 7/1989 | European Pat. Off. . |
| 0 353 972A | 2/1990 | European Pat. Off. . |
| 0353972 A1 | 2/1990 | European Pat. Off. . |
| 2 283 916 | 10/1993 | United Kingdom . |

OTHER PUBLICATIONS

WO 91/01706 International Application.
WO 89/05619 International Application.
WO 94/15562 International Application.

*Primary Examiner*—Thurman K. Page
*Assistant Examiner*—Kathryne E. Shelborne
*Attorney, Agent, or Firm*—Tilton Fallon Lungmus

[57] ABSTRACT

An adhesive wafer, which is especially suitable for use as a faceplate for an ostomy appliance but may also be used as a wound dressing, has an adhesive layer of hydrocolloid-containing skin barrier material and a flexible backing layer extending over one surface of the adhesive layer. The opposite skin-contacting surface of the adhesive layer is embossed to provide a pattern of discrete, non-connecting depressions separated and isolated from each other by flat-topped ridges dimensioned and arranged so that a skin surface engaged by said embossed surface primarily contacts only such ridges.

25 Claims, 2 Drawing Sheets

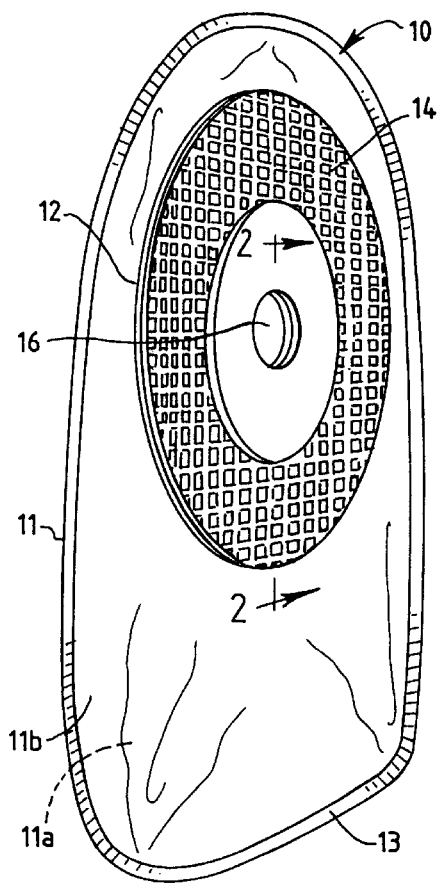
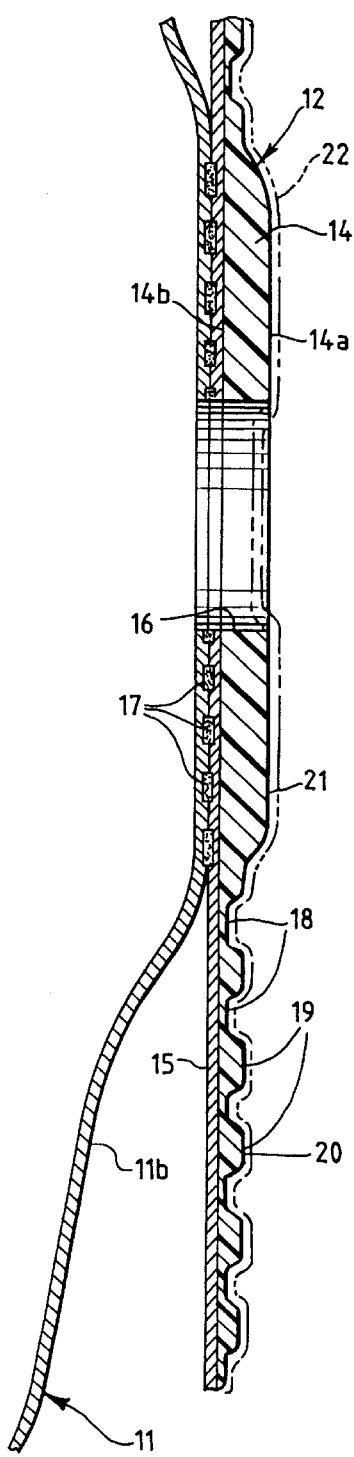
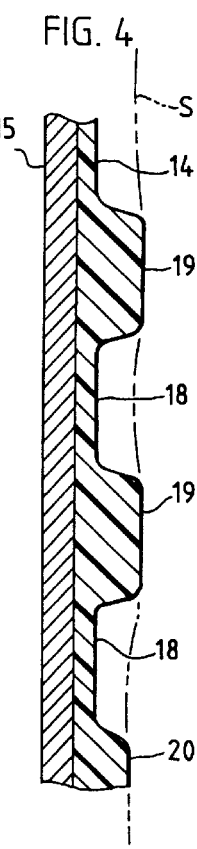
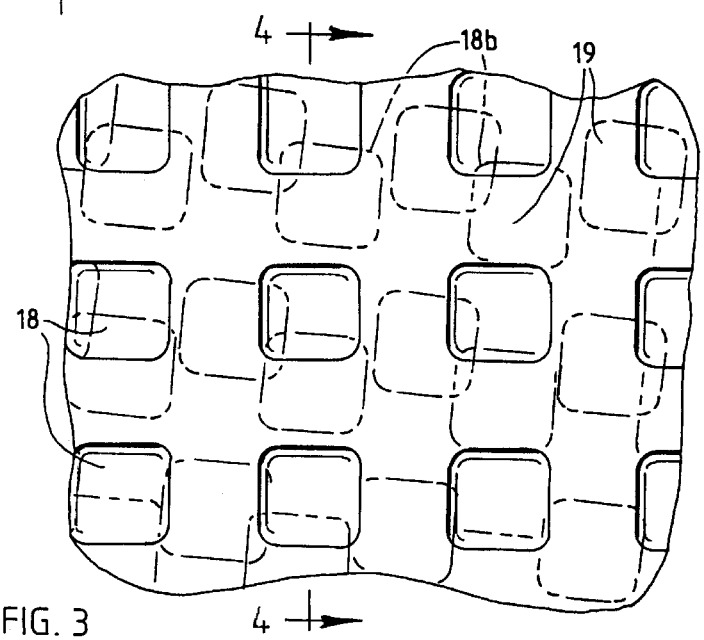

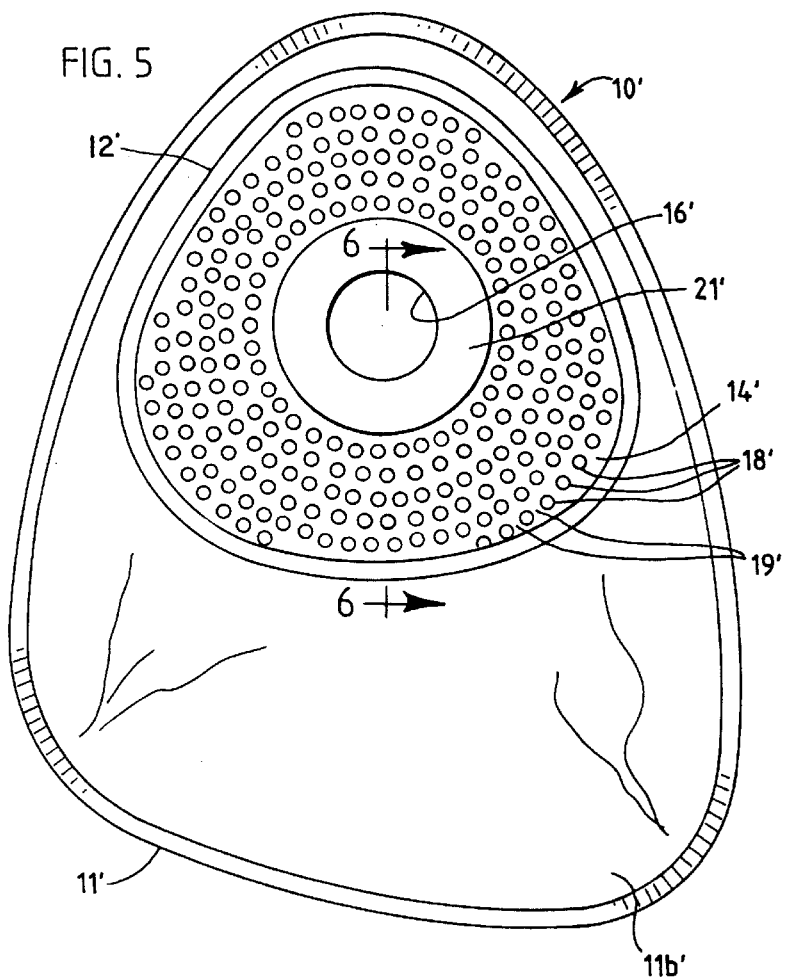
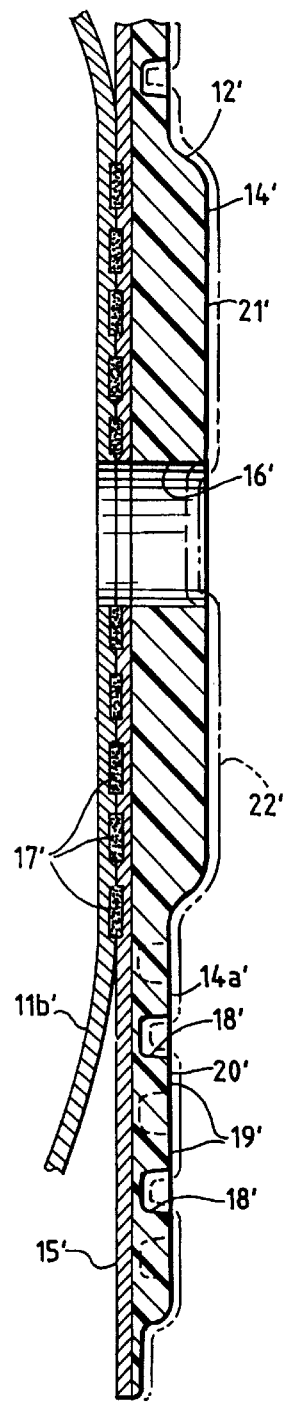
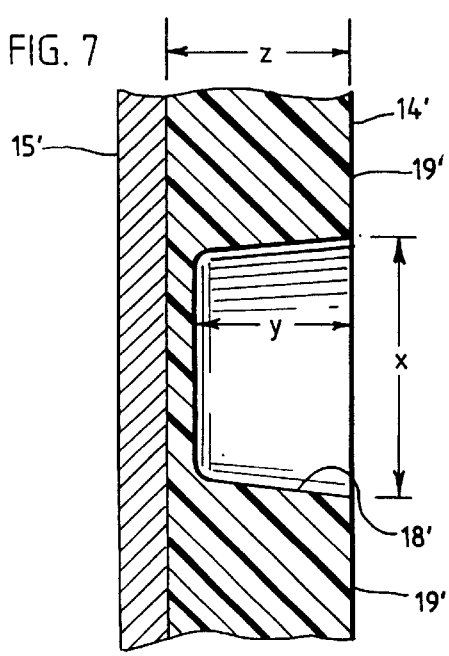

ADHESIVE WAFER WITH EMBOSSED SKIN-CONTACTING SURFACE

BACKGROUND AND SUMMARY

Adhesive wafers in which the adhesive material has hydrocolloid particles dispersed therein, and is moisture absorbing as well as providing both dry and wet tack, are well known for use as wound dressings and as the attachment faceplates for ostomy appliances. Efforts have been made to formulate the adhesive compositions so that they are skin-friendly— that is, are generally non-irritating to the skin and minimize the possibilities of damage to the skin when the adhesive wafers are removed and replaced. Nevertheless, irritation and injury to the skin often occur, sometimes even resulting in a stripping away of surface layers of the skin, when such a wafer is removed and replaced on a daily basis (or even more frequently), and such problems are exacerbated by the need to replace a removed wafer with a fresh one onto the same skin surfaces.

A main aspect of this invention therefore lies in providing a wafer having an occlusive skin-contacting adhesive surface that is embossed in such a way as to limit the extent of surface contact with the skin and, even more significantly, to render it unlikely that the same skin surfaces will be contacted to the same extent when the wafer is removed and replaced by a fresh wafer. Specifically, the bodyside surface of the wafer's adhesive layer is embossed to provide a pattern of small, discrete, non-connecting depressions or recesses separated and isolated from each other by flat-top skin-contacting ridges. When the wafer is in place, a skin surface engaged by the embossed surface primarily contacts only the ridges. The surface of the skin tends to bridge the depressions, with the result that only a fraction of the area of the embossed surface directly contacts the skin. The pattern of embossing renders it highly unlikely that only the skin areas contacted by a removed wafer will again be contacted by a fresh replacement wafer, since even slight lateral or rotational displacement in the position of the fresh wafer will bring its ridges into adhesive contact with skin surfaces not engaged by the previous wafer. The result is a wafer of enhanced skin friendliness which promotes healing, or at least avoids or reduces irritation, of the isolated skin areas underlying the depressions and which eliminates or reduces the possibilities that surface layers of skin will be stripped away as the adhesive wafer is removed.

The surface of the adhesive layer opposite from the embossed surface is covered by a flexible backing layer. The material of the backing layer may vary depending in part on whether the wafer is used as a wound dressing or as the faceplate of an ostomy appliance. The backing layer may take the form of a moisture-impervious film, such as an elastomeric film, or it may be composed of a porous material such as an open-cell foam or a non-woven fabric.

In one embodiment of the invention, the wafer comprises the faceplate of an ostomy appliance which includes a collection pouch having a side wall opening. The wafer is also provided with an opening, and the wafer's backing layer and the pouch are secured together, such as by an annular heat seal, in an area surrounding the aligned openings. Also, in such preferred embodiment, the bodyside surface of the wafer has a non-embossed annular portion immediately surrounding the wafer's stoma-receiving opening.

Other features, advantages and objects of the invention will become apparent from the specification and drawings.

DRAWINGS

FIG. 1 is a perspective view of one embodiment of an ostomy appliance having an embossed wafer as the faceplate thereof.

FIG. 2 is an enlarged fragmentary sectional view taken along line 2—2 of FIG. 1.

FIG. 3 is an enlarged fragmentary plan view of the bodyside surface of the wafer with the release sheet removed therefrom for clarity of illustration.

FIG. 4 is a still further enlarged fragmentary sectional view taken along line 4—4 of FIG. 3.

FIG. 5 is a front elevational view of an ostomy appliance constituting a second embodiment of the invention.

FIG. 6 is an enlarged sectional view taken along line 6—6 of FIG. 5.

FIG. 7 is a greatly enlarged sectional view illustrating certain dimensional relationships of a preferred embodiment.

DETAILED DESCRIPTION OF PREFERRED EMBODIMENTS

A wafer embodying this invention may be used by itself as a wound dressing, but the advantages of its construction and operation are found particularly apparent when such a wafer is combined with a collection pouch to function as an improved ostomy appliance. The wafer is therefore shown in the drawings attached to a collection pouch, with such usage of the wafer constituting a preferred embodiment.

Referring to the drawings, the numeral 10 generally designates an ostomy appliance comprising a pouch 11 and an adhesive wafer 12 serving as the faceplate for adhesively attaching the appliance to the peristomal skin surfaces of a patient. The pouch 11 is conventional, being essentially composed of a pair of side walls 11a and 11b of thermoplastic film sealed to each other along their edges 13 as indicated in FIG. 1. While the pouch is shown as being sealed along all of its edges, it may if desired be provided with a drainage opening at its lower end. Such opening, if provided, may be closed by a suitable clamp of the type disclosed in U.S. Pat. No. 3,523,534 or, alternatively, may be equipped with a valve as disclosed, for example, in U.S. Pat. Nos. 3,598,150 and 4,280,498. The pouch may be formed of a film composed of any suitable heat-sealable plastic or a combination of plastics (e.g., as a coextruded laminate) that is tough, flexible, and liquid and gas impermeable, all as well known in the art. One such film found to be particularly effective is a coextrusion of polyethylene and polyvinylidene chloride available under the trademark "Saranex" from Dow Chemical, Midland, Mich., but other films having similar properties may be used.

Wafer 12 is in the form of a disc which is illustrated in FIG. 1 as being generally circular in shape but, if desired, may assume other configurations. As shown in FIG. 2, the wafer essentially comprises an occlusive adhesive layer 14 and a backing layer 15. The adhesive layer is generally planar and has a front or bodyside surface 14a and a rear or back surface 14b. The flexible backing layer 15 covers the back surface 14b of the adhesive layer as shown in FIG. 2. A centrally-located stoma-receiving opening 16 extends through both layers and serves as a starter opening which may be enlarged by the user (with scissors) to provide a re-formed opening that is sized and configured to match a patient's stoma.

The backing layer 15 may be unitary (as shown) or may itself consist of multiple layers. It must be flexible and may be stretchable and contractable for purposes of anatomical conformity. It should also be heat-sealable, especially where the wafer is to function as an ostomy faceplate as shown. The backing layer may be in the form of a film of polyurethane, polyethylene, or other suitable thermoplastic material. Alternatively, it may be a soft, flexible thermoplastic foam of closed, semi-open, or fully-open cell construction. Polyurethane or polyethylene foams are believed suitable, but other thermoplastic foams having similar properties may be used. Particularly effective results for purposes of an ostomy appliance are obtained where the backing layer 15 is formed of a soft, porous non-woven fabric of thermoplastic fibers such as, for example, a non-woven fabric of spun-bonded polyethylene fibers. One such fabric is marketed under the designation P80-00 by Corovin GmBh, Peine, Germany, but other non-woven fabrics having similar properties may be used.

The backing layer 15 is permanently joined to wall 11b of the pouch 11 by heat seals 17 that surround stoma-receiving opening 16. The heat seal may take the form of a multiplicity of concentric heat seals as shown. Alternatively, the connection may take the form of a single continuous annular heat seal. In any case, the heat seal area should be dimensioned and located so that a user may enlarge the opening 16 without destroying the integrity of the seal between the wafer and pouch.

Adhesive layer 14 is of a moisture-absorbing and moisture-swellable skin barrier material having a continuous phase composed of one or more tacky elastomers and a discontinuous phase consisting essentially of one or more hydrocolloids dispersed throughout the adhesive layer. Typical hydrocolloids are pectin, gelatin and sodium or calcium carboxymethylcellulose, but other hydrocolloids such as karaya may be used. If desired, superabsorbents may also be included in the barrier formulation. The continuous elastomeric phase may be composed of a tacky, deformable elastomeric material such as polyisobutylene and/or a block copolymer such as a styrene-isopyrene-styrene copolymer of the type described in U.S. Pat. Nos. 4,738,257 and 4,231,369. Tackifiers, plasticizers, extenders and stabilizers may be included, all as well known in the art. One example of a barrier composition suitable for use for adhesive layer 14 is disclosed in aforementioned U.S. Pat. No. 4,738,257, but other hydrocolloid-containing compositions known for use or ostomy faceplates and wound dressings may be used.

A characteristic feature of wafer 12 lies in the fact that the bodyside surface 14a of adhesive layer 14 is embossed to provide a pattern of discrete, non-connecting depressions or recesses 18 separated and isolated from each other by ridges or shoulders 19. The ridges are flat-topped for adhesively contacting and sealingly-engaging a skin surface surrounding a stoma or wound. The flat tops of the ridges are generally coplanar with each other, and the depressions 18 are sufficiently deep so that when the wafer is in use the skin surface S contacted by the adhesive layer 14 tends to bridge the depressions as depicted in phantom in FIG. 4.

FIG. 3 shows depressions 18 as being generally square in shape, giving the embossed surface a waffle-like pattern or appearance but, if desired, the depressions may be circular or assume other shapes as long as such depressions do not communicate with each other and the ridges 19 are dimensioned and arranged to prevent outward (radial) flow of fluids between stoma opening 16 and the outer peripery of the wafer. Also, while the depressions are shown as being of uniform size and shape, both the shapes and the sizes may vary, if desired. In general, it is believed advantageous if the combined area of the depressions is approximately equal to the combined area of the flat top surfaces of the ridges, although considerable variation in that relationship is permissible.

In the embodiment illustrated in FIGS. 1–4, the embossing is provided only along an outer portion 20 of the wafer that surrounds an inner non-embossed portion 21. The thickness of the non-embossed portion 21 should be at least as great as the thickness (i.e, axial extent) of the ridges 19 of the embossed portion 20; in the illustration given, the thickness of portion 21 is substantially greater to enhance the moisture-absorbing capacity of the annular zone immediately surrounding the stoma-receiving opening 16. As shown in the drawings, the bodyside surface of the non-embossed portion 21 is smooth to insure greater sealing effectiveness with the skin surfaces immediately surrounding a patient's stoma.

The drawings depict the wafer 12 in a condition in which it would be ready for use, with the bodyside surface of the adhesive layer 14 exposed for contact with a patient's skin. To protect the adhesive surface during storage and handling prior to use, bodyside surface 14a is covered by a release sheet or panel 22 shown in phantom in FIG. 2. The release sheet 22 may be formed of siliconized paper or any other suitable material that will provide the protective effects and allow the sheet to be peeled away from the adhesive layer when the wafer is being readied for application. Particularly effective results have been achieved by forming the sheet or panel 22 of a relatively stiff shape-retaining thermoplastic material such as polyethylene and by forming or preforming the sheet or panel so that it matches the surface contours of the adhesive layer, including the depressions or recesses of that layer. By so doing, the ridges and depressions of the soft, pliant adhesive layer will be more readily retained in their desired shapes until the time of use.

FIG. 3 schematically illustrates some of the important advantages achieved by embossing the bodyside surface of the adhesive layer. When an ostomate removes an appliance and replaces it with a fresh appliance, it is unlikely that the orientation of the new wafer will be precisely identical to that of the wafer being replaced. Slight differences in orientation may take the form of lateral displacement or rotational displacement. In either case, the skin surfaces contacted by the ridges of the replacement wafer will almost invariably differ to some extent from the surfaces contacted by the prior wafer. If the depressions 18 of the prior wafer were oriented as represented by solid lines in FIG. 3, then those of the replacement wafer might assume (for example) the positions depicted by broken lines 18a or 18b. The result is that the ridges 19 of the replacement wafer that make sealing contact with the patient's skin will tend to contact areas of the skin that previously were located at least partially beneath the depressions 18 of the prior wafer. Because the embossed surface of the wafer makes only limited surface contact with the skin, and because the contact areas of a replacement wafer will not be entirely the same as those contacted by the prior wafer, the patient's skin is less subject to irritation and stripping effects than if the wafer surfaces were non-embossed. The embossing therefore enhances the skin-friendliness of the wafer and reduces the possibilities of patient discomfort and injury.

While the wafer is shown in conjunction with an ostomy pouch, it will be understood that the advantages of providing the adhesive surface 14a with ridges and depressions might be achieved if the wafer were instead used as an occlusive wound dressing. In that event, stoma opening 16 and pouch 11 would be omitted and, if desired, the entire bodyside surface of the adhesive layer would be embossed. Alternatively, a wound dressing might be provided in which the bodyside surface of the adhesive layer overlying the wound is not embossed and such embossing is provided only along the adhesive surfaces of the dressing that contact the healthy skin areas surrounding the wound.

FIGS. 5–7 depict a second embodiment of the invention which is similar in essential respects to the embodiment of FIGS. 1–4. Ostomy appliance 10' includes pouch 11' and wafer 12', with the wafer similarly comprising an adhesive layer 14' and a backing layer 15'. The compositions of the adhesive and backing layers may be the same as those already disclosed and, as shown in FIG. 6, the backing layer 15' is heat sealed at 17' to the bodyside wall 11b' of pouch 11'. A stoma-receiving opening 16' extends through the central portion of the wafer and into pouch 11'. As in the first embodiment, the wafer 12' has a relatively thick non-embossed central portion 21' surrounded by an outer embossed portion 20'. To protect the adhesive surface during storage and handling, the bodyside surface 14a' is covered by a release sheet or panel 22' that is formed or preformed to match the contour of the wafer and thereby prevent the soft, pliant material of adhesive layer 14' from a flowing action or deforming forces that might otherwise alter and even obliterate the depressions of the embossed surface.

As shown most clearly in FIG. 5, the depressions 18' are circular rather than square and are arranged in what appears as a random pattern about the raised central portion 21'. Unlike the grid arrangement of the first embodiment, the pattern is not rectilinear, meaning that the depressions 18' are not arranged along straight perpendicular lines. As a result, the forces required to peel wafer 12' away from the skin tend to be relatively uniform since the ridges or shoulders 19' that contact the patient's skin extend in many different directions. Therefore, the wafer may be removed from the skin with a smooth peeling action and without the changes in resistance that might occur if the depressions were arranged in a rectilinear grid pattern and the peeling force happened to extend along one of the axes of the grid. The smoothness of the peeling action is believed to cause less discomfort for the patient and further reduce the possibilities of skin irritation and injury.

As in the prior embodiment, ridges or shoulders 19' are flat topped and coplanar when the wafer is in the flat condition shown in the drawings. The depressions 18' are non-communicating to prevent channeling and leakage and are dimensioned and arranged to make it highly unlikely that the depressions and ridges of a replacement wafer will assume the same positions in relation to the skin as those of the wafer being replaced. The skin-friendliness of the wafer is thereby enhanced in the manner previously described.

In all preferred embodiments of the invention, it is believed that the depressions should have dimensions and size relationships that reduce the possibilities of the skin making adhesive contact with the barrier material within the depressions and also reduce the possibilities that the depressions will become closed or obliterated by deformation of the adhesive material while the wafer is being worn. Some barrier materials are softer, more pliant, and more subject to flow and deformation than others but, in general it is believed that the measurement across the opening of each depression, represented as "x" in FIG. 7, should fall within the range of about 0.5 mm (0.0197") to 7 mm (0.275"). The depth "y" of each depression should be less than the thickness of the embossed portion of the adhesive layer (dimension "z") but should be at least 20% of dimension "x."

While in the foregoing we have disclosed embodiments of the invention in considerable detail for purposes of illustration, it will be understood by those skilled in the art that many of these details may be varied without departing from the spirit and scope of the invention.

We claim:

1. An adhesive wafer for an ostomy faceplate or wound dressing, comprising an adhesive layer of moisture-absorbing skin barrier material having a continuous phase composed of a tacky elastomer and a discontinuous phase consisting essentially of one or more moisture-absorbing and swellable hydrocolloids dispersed in said continuous phase; said adhesive layer having a bodyside surface for direct contact with a patient's skin and a back surface opposite from said bodyside surface; and a flexible backing layer covering said back surface of said adhesive layer; wherein the improvement comprises said adhesive layer having at least a portion of said bodyside surface thereof embossed to provide a pattern of discrete, non-connecting depressions separated and isolated from each other by skin-contacting ridges dimensioned and arranged so that a skin surface engaged by said embossed surface primarily contacts only said ridges of said adhesive and wherein said ridges have flat and generally co-planar skin-contacting surface portions.

2. The wafer of claim 1 wherein said wafer constitutes an ostomy faceplate and has a centrally-located stoma-receiving opening therein.

3. The wafer of claim 2 in which said bodyside surface of said adhesive layer includes a non-embossed annular portion surrounding said stoma-receiving opening and said embossed portion of said bodyside surface surrounds said non-embossed annular portion.

4. The wafer of claim 3 wherein said non-embossed annular portion defines a generally planar surface spaced from said back surface a distance no less than the distance between said back surface and the skin-contacting surface portions of said ridges.

5. The wafer of claim 1 wherein said depressions are arranged in a rectilinear waffle pattern.

6. The wafer of claim 1 wherein said depressions are arranged in a non-rectilinear pattern of random appearance.

7. The wafer of claim 1 wherein at least some of said depressions are generally square in outline.

8. The wafer of claim 1 wherein at least some of said depressions are generally round in outline.

9. The wafer of claim 1 in which each of said depressions has a width within the range of about 0.5 mm to about 7 mm.

10. The wafer of claim 9 wherein the depth of each said depressions is less than the thickness of the embossed portion of said adhesive layer and at least 20% of the width of said depression.

11. The wafer of claim 1 wherein said flexible backing layer is gas pervious.

12. The wafer of claim 11 wherein said backing layer comprises a porous non-woven fabric.

13. The wafer of claim 1 in which a removable protective release sheet covers said bodyside surface of said adhesive layer.

14. The wafer of claim 13 in which said release sheet includes ridges and depressions that conform with the embossed contour of said bodyside surface of said adhesive layer.

15. An ostomy appliance comprising a wafer and a collection pouch; said collection pouch having a side wall with a stoma-receiving opening therein; said wafer comprising an adhesive layer of moisture-absorbing skin barrier material having a continuous phase composed of a tacky elastomer and a discontinuous phase consisting essentially of one or more moisture-absorbing and swellable hydrocolloids dispersed in said continuous phase; said adhesive layer having a bodyside surface for direct contact with a patient's skin and a back surface opposite from said bodyside surface; said wafer also including a flexible thermoplastic backing layer covering said back surface of said adhesive layer; said wafer having a stoma-receiving opening aligned with the opening of said pouch and said backing layer of said wafer being sealed to said pouch in an annular sealing zone immediately surrounding the stoma-receiving openings of said wafer and pouch; wherein the improvement comprises said adhesive layer having at least a portion of said bodyside surface thereof embossed to provide a pattern of discrete, non-connecting depressions separated and isolated from each other by skin-contacting ridges dimensioned and arranged to that a skin surface engaged by said embossed surface primarily contacts only said ridges of said adhesive and wherein said ridges have flat and generally co-planar skin-contacting surface portions.

16. The appliance of claim 15 in which said bodyside of surface of said adhesive layer includes a non-embossed annular position immediately surrounding said stoma-receiving opening of said wafer; said embossed portion of said adhesive layer surrounding said non-embossed annular portion.

17. The appliance of claim 16 in which said non-embossed annular portion of said adhesive layer defines a generally planar surface spaced from said back surface of said adhesive layer a distance no less that the distance between said back surface and the skin-contacting surface portions of said ridges.

18. The appliance of claim 15 wherein said depressions are arranged in a rectilinear waffle pattern.

19. The appliance of claim 15 wherein said depressions are arranged in a non-rectilinear pattern of random appearance.

20. The appliance of claim 15 wherein at least some of said depressions are generally square in outline.

21. The appliance of claim 15 wherein at least some of said depressions are generally round in outline.

22. The appliance of claim 15 in which each of said depressions has a width within the range of about 0.5 mm to about 7 mm.

23. The appliance of claim 22 wherein the depth of each said depression is less than the thickness of the embossed portion of said adhesive layer and at least 20% of the width of said depression.

24. The appliance of claim 15 in which a removable protective release sheet covers said bodyside surface of said adhesive layer.

25. The appliance of claim 24 in which said release sheet includes ridges and depressions that conform with the embossed contour of said bodyside surface of said adhesive layer.

* * * * *